United States Patent
Zazovsky et al.

(10) Patent No.: US 9,574,938 B2
(45) Date of Patent: Feb. 21, 2017

(54) SAMPLING TOOL WITH DUAL FLOWLINE ARCHITECTURE

(75) Inventors: Alexander F. Zazovsky, Houston, TX (US); Mark Milkovisch, Cypress, TX (US); Toru Terabayashi, Kanagawa-ken (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 759 days.

(21) Appl. No.: 13/996,491

(22) PCT Filed: Dec. 22, 2011

(86) PCT No.: PCT/US2011/066844
§ 371 (c)(1),
(2), (4) Date: Jun. 20, 2013

(87) PCT Pub. No.: WO2012/088417
PCT Pub. Date: Jun. 28, 2012

(65) Prior Publication Data
US 2013/0293891 A1 Nov. 7, 2013

Related U.S. Application Data

(60) Provisional application No. 61/426,573, filed on Dec. 23, 2010.

(51) Int. Cl.
*E21B 49/10* (2006.01)
*G01J 3/02* (2006.01)
(Continued)

(52) U.S. Cl.
CPC ............ *G01J 3/0267* (2013.01); *E21B 49/008* (2013.01); *E21B 49/10* (2013.01); *E21B 2049/085* (2013.01)

(58) Field of Classification Search
CPC .. E21B 49/08; E21B 49/081; E21B 2049/085; E21B 49/10
See application file for complete search history.

(56) References Cited

U.S. PATENT DOCUMENTS

| | | | | |
|---|---|---|---|---|
| 4,994,671 A * | 2/1991 | Safinya | ................. | E21B 47/102 250/253 |
| 5,859,430 A * | 1/1999 | Mullins | ................. | E21B 47/102 250/255 |

(Continued)

OTHER PUBLICATIONS

International Search Report for International Application No. PCT/US2011/06844 dated Sep. 27, 2012.

(Continued)

*Primary Examiner* — Elizabeth Gitlin

(57) ABSTRACT

An optical fluid analyzer tool may have an evaluation flowline which receives a flow of fluid from a geotechnical formation and may have a cleanup flowline which receives another flow of fluid from the geotechnical formation. A flow routing system may be connected to the evaluation flowline and may be connected to the cleanup flowline. The flow routing system may establish isolated flow or commingled flow for the evaluation flowline and may establish isolated flow or commingled flow for the cleanup flowline. A sample chamber may be connected to the evaluation flowline and may be connected to the cleanup flowline. A first pump module may draw the fluid from the geotechnical formation, and an optical fluid analyzer connected to the cleanup flowline and the evaluation flowline may analyze the fluid.

18 Claims, 15 Drawing Sheets

(51) Int. Cl.
*E21B 49/00* (2006.01)
*E21B 49/08* (2006.01)

(56) References Cited

U.S. PATENT DOCUMENTS

| | | | |
|---|---|---|---|
| 7,178,591 B2 | 2/2007 | Del Campo et al. | |
| 7,484,563 B2 | 2/2009 | Zazovsky et al. | |
| 7,654,321 B2 | 2/2010 | Zazovsky et al. | |
| 7,841,406 B2 * | 11/2010 | Zazovsky | E21B 49/10 166/100 |
| 2003/0042021 A1 | 3/2003 | Bolze et al. | |
| 2008/0073078 A1 | 3/2008 | Sherwood | |
| 2010/0018704 A1 | 1/2010 | Zazovsky et al. | |
| 2010/0307769 A1 | 12/2010 | Briquet et al. | |

OTHER PUBLICATIONS

Examiner's Report for Canadian Application No. 2821899 dated Oct. 27, 2014.

* cited by examiner

SAMPLING TOOL WITH DUAL FLOWLINE ARCHITECTURE

This application claims the benefit of U.S. Provisional Application Ser. No. 61/426,573 entitled "Optical Fluid Analyzer With Dual Flowline Architecture For Contamination Monitoring" filed Dec. 23, 2010.

BACKGROUND

Optical fluid analyzers are used to analyze fluid obtained from downhole environments to aid operators in drilling and hydrocarbon recovery operations. A reservoir is a subterranean formation which has porosity and permeability which enable the formation to store and transmit fluids. Downhole fluid analysis may provide real-time information about the composition of a subterranean formation and/or fluids in a subterranean formation. Such real-time information may be used to improve or optimize the effectiveness of formation testing tools during sampling processes in a given well. For example, downhole fluid composition analysis may reduce the number of samples obtained and sent to the surface for further analysis.

More generally, accurate data about the characteristics of a formation fluid, such as a reservoir fluid, enables predictions about the subterranean formation. Thus, the accuracy of the data impacts reservoir performance, such as, for example, production, quality, volume, efficiency and the like.

It remains desirable to provide improvements in optical fluid analyzers and methods of using optical fluid analyzers.

DETAILED DESCRIPTION

The present disclosure generally relates to an optical fluid analyzer with a dual flowline architecture and a flow routing system. The optical fluid analyzer may use two flowlines for fluid optical density monitoring and may use the flow routing system to alternate flows from sample intakes and guard intakes through the two flowlines. The flow routing system may establish isolated flow or commingled flow for the evaluation flowline and may establish isolated flow or commingled flow for the cleanup flowline.

The optical fluid analyzer may have a housing traversed at least partially by two flowlines having inlet ports. The optical fluid analyzer may have two sensors disposed in the housing. Each of the sensors may be coupled to one of the two flowlines, and the sensors may share a signal transducer. The optical fluid analyzer may have a commingle/split flow router disposed in the housing upstream from the two sensors, and the router may fluidly couple one of the two flowlines to the two sensors. The optical fluid analyzer may have a processor to correct for the different time of flow in the two flowlines between the inlet port and the sensor. The signal transducer may be a lamp which emits light in the visible/near infra-red range, an optical filter in the visible/near infra-red range, a lens and a photodiode, a frequency filter, an oscillator, a synthesizer, an equalizer, and/or the like.

Figure 1:
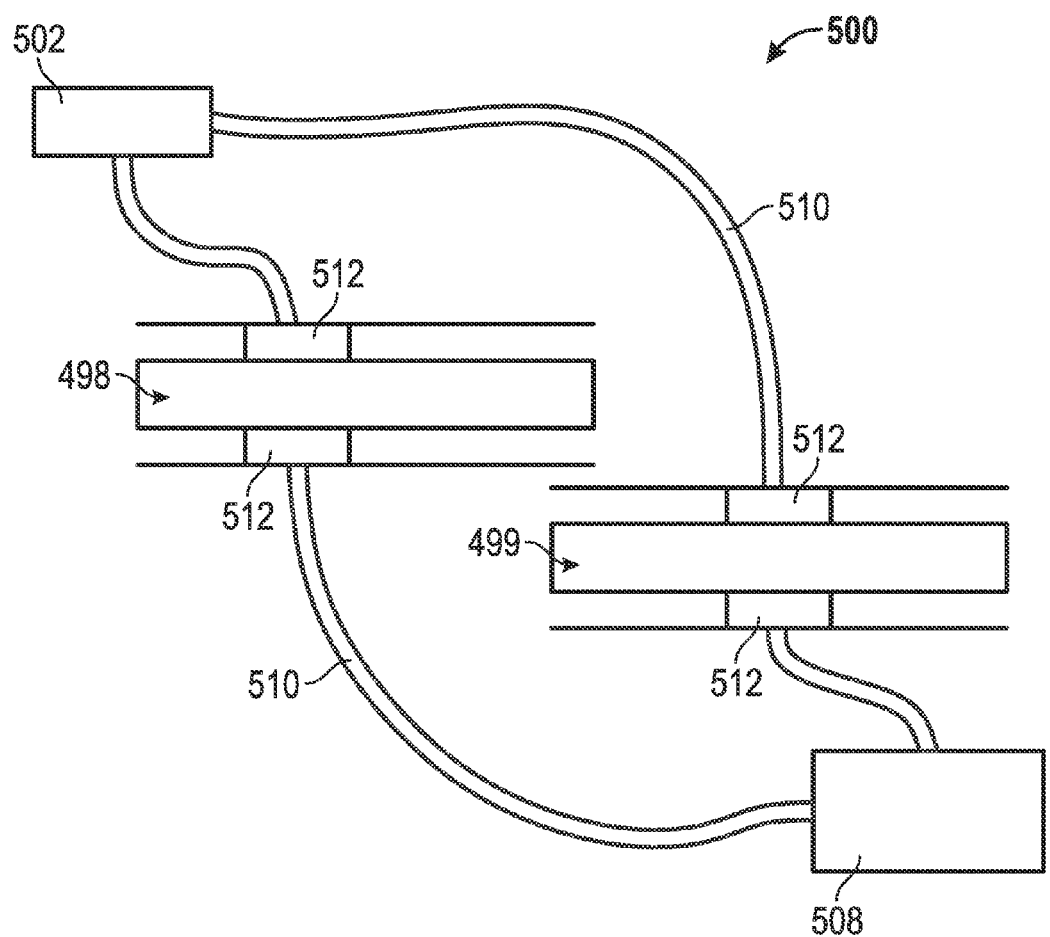
FIG. 1 generally illustrates an example of a single optical fluid analyzer in accordance with one or more aspects of the present disclosure.

FIG. 1 generally illustrates an embodiment of a single optical fluid analyzer module 500 with a first flowline 498 and a second flowline 499. Optical illumination may be provided by a lamp 502. Optical fiber bundles 510 may be connected to the lamp 502, optical windows 512 on the first flowline 498 and the second flowline 499, and a spectrometer 508. The spectrometer 508 may be positioned to measure light passing through the optical fiber bundles 510. In some embodiments, the single optical fluid analyzer module 500 may have only one spectrometer 508 so that the one spectrometer 508 may analyze and/or may obtain measurements for the first flowline 498 and the second flowline 499 substantially simultaneously. However, other embodiments of the single optical fluid analyzer module 500 may have more than one spectrometer 508.

Figure 2:
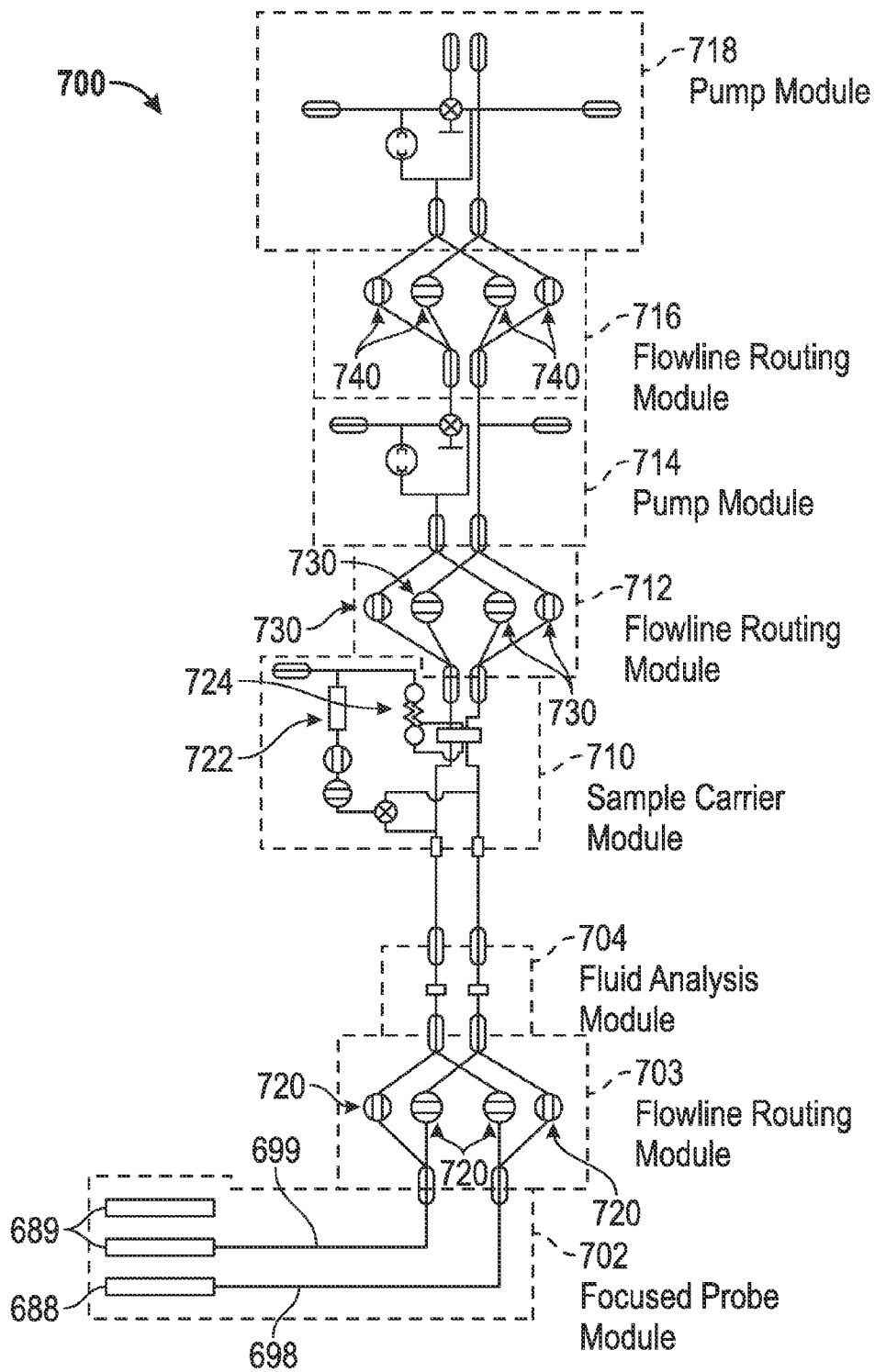
FIGS. 2-21 generally illustrate examples of tool strings employing a single optical fluid analyzer in accordance with one or more aspects of the present disclosure.

FIG. 2 generally illustrates an example of a sampling tool 700 which may employ embodiments of the single optical fluid analyzer module 500. The sampling tool 700 may be a packer which may expand against the surrounding wellbore wall to isolate a region of the wellbore and/or may abut a geotechnical formation to withdraw fluid from the geotechnical formation. For example, the sampling tool 700 may have flexible, elastomeric elements that expand. The sampling tool 700 may attach and/or detach from a drill string. Such additions and/or subtractions may be made through an adapter sub, for example.

The sampling tool 700 may have a focused probe module 702 which may withdraw fluid from a geotechnical formation. The focused probe module 702 may obtain fluid from the geotechnical formation through an evaluation flowline 698 and a cleanup flowline 699. In an embodiment, the evaluation flowline 698 and the cleanup flowline 698 may be made of one or more stainless steel materials; however, the evaluation flowline 698 and the cleanup flowline 698 may be made of any material.

Flow may be initiated by a first pump module 714 and/or the second pump module 718. In an embodiment, the first pump module 714 and/or the second pump module 718 may be located at and/or proximate to the top of the sampling tool 700; however, the first pump module 714 and/or the second pump module 718 may be located at any position in the sampling tool 700.

The evaluation flowline 698 may be connected to a sample inlet 688 which collects virgin fluid, and the cleanup flowline 699 may be connected to one or more guard inlets 689 which collect contaminated fluid. The sample inlet 688 may be positioned at or near the distal end of the focused probe module 702 to obtain samples of clean formation fluid from the connate fluid zone. The one or more guard inlets 689 may be positioned a distance from the distal end of the focused probe module 702 to draw contaminated fluid from the invaded zone into the sampling tool 700 and away from the sample inlet 688. However, the sampling tool 700 is not limited to specific locations of the sample inlet 688 and the one or more guard inlets 689.

The fluids in the evaluation flowline 698 and/or the cleanup flowline 699 may then travel through a first flowline routing module 703 that may convey the fluids to a fluid analysis module 704. The first flowline routing module 703 may use internal valves 720 to provide separate flow in the evaluation flowline 698 and the cleanup flowline 699 relative to each other. The first flowline routing module 703 may use the internal valves 720 to interchange the fluids between the evaluation flowline 698 and the cleanup flowline 699. For example, the first flowline routing module 703 may convey fluids from the cleanup flowline 699 into the evaluation flowline 698, and/or the first flowline routing module 703 may convey fluids from the evaluation flowline 698 into the cleanup flowline 699. The first flowline routing module 703 may use the internal valves 720 to prevent fluid flow into the focused probe module 702.

The fluid analysis module 704 may be the single optical fluid analyzer module 500 and/or another optical fluid analyzer module. After the fluids travel through the fluid analysis module 704, the fluids may enter a sample carrier module 710 that may have a sample chamber 722 and/or a relief valve 724. The relief valve 724 may relieve pressure within the evaluation flowline 698 and/or the cleanup flowline 699 if pressure exceeds a predefined limit or an operator wishes to reduce pressure.

The sample carrier module 710 may use the sample chamber 722 to obtain and/or store fluid samples for analysis. The sample chamber 722 may have analysis capabilities which may be remotely activated for analysis of the fluid samples. The sample chamber 722 may be removable from the sampling tool 700 and/or may have a separate port from which fluid may be withdrawn. A second flowline routing module 712 may be positioned above the sample carrier module 710 and may enable the first pump module 714 to draw fluid into the evaluation flowline 698 or the cleanup flowline 699.

The second flowline routing module 712 may use internal valves 730 to provide separate flow in the evaluation flowline 698 and the cleanup flowline 699 relative to each other. The second flowline routing module 712 may use the internal valves 730 to interchange the fluids between the evaluation flowline 698 and the cleanup flowline 699. For example, the second flowline routing module 712 may convey fluids from the cleanup flowline 699 to the evaluation flowline 698, and/or the second flowline routing module 712 may convey fluids from the evaluation flowline 698 into the cleanup flowline 699. The second flowline routing module 712 may use the internal valves 730 to prevent fluid flow into the focused probe module 702.

A third flowline routing module 716 may be positioned above the first pump module 714 and may enable the second pump module 718 to draw fluid into the evaluation flowline 698 or the cleanup flowline 699. The first pump module 714 and the second pump module 716 may be any pump that withdraws a fluid from the geotechnical formation for analysis in the fluid analysis module 704 and/or the sample chamber 722. The first pump module 714 and/or the second pump module 716 may have a port from which fluid may be withdrawn.

The third flowline routing module 716 may use internal valves 740 to provide separate flow in the evaluation flowline 698 and the cleanup flowline 699 relative to each other. The third flowline routing module 716 may use the internal valves 740 to interchange the fluids between the evaluation flowline 698 and the cleanup flowline 699. For example, the third flowline routing module 716 may convey fluids from the cleanup flowline 699 into the evaluation flowline 698, and/or the third flowline routing module 716 may convey fluids from the evaluation flowline 698 into the cleanup flowline 699. The third flowline routing module 716 may use the internal valves 740 to prevent fluid flow into the focused probe module 702.

Figure 3:
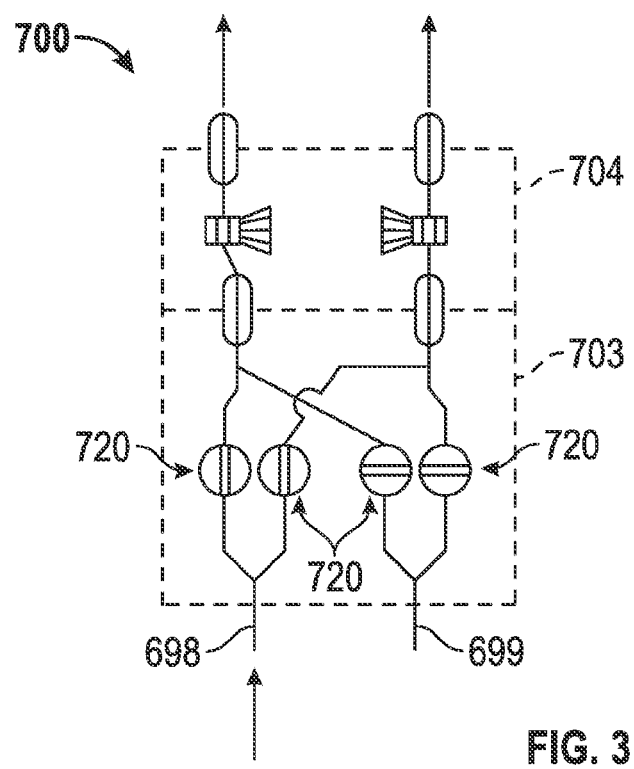
Figure 4:
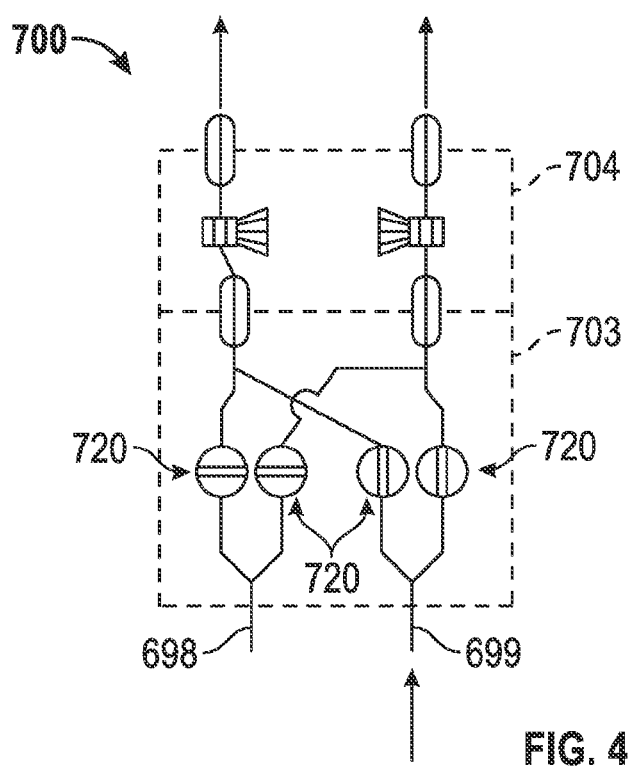

FIGS. 3 and 4 generally illustrate split flow for dual flowline monitoring in the sampling tool 700 after commingling the flow. As shown in FIG. 3, the valves 720 may direct fluid in the evaluation flowline 698 into the cleanup flowline 699 and the subsequent section of the evaluation flowline 698. As shown in FIG. 4, the valves 720 may direct fluid in the cleanup flowline 699 into the evaluation flowline 698 and the subsequent section of the cleanup flowline 699.

Such embodiments may be used to create a self-calibrating optical monitoring system because the composition of fluids in both monitoring flowlines may be substantially the same. For example, as shown in FIG. 3, the fluid analysis module 704 may be calibrated based on measurements obtained when a portion of the fluid withdrawn through the evaluation flowline 698 is routed into the fluid analysis module 704 in the evaluation flowline 698 and a portion of the fluid withdrawn through the evaluation flowline 698 is routed into the fluid analysis module 704 in the cleanup flowline 699. The portion of the fluid withdrawn through the evaluation flowline 698 which is routed into the fluid analysis module 704 in the evaluation flowline 698 may be routed substantially simultaneously to routing of the portion of the fluid withdrawn through the evaluation flowline 698 which is routed into the fluid analysis module 704 in the cleanup flowline 699.

As another example, as shown in FIG. 4, the fluid analysis module 704 may be calibrated based on measurements obtained when a portion of the fluid withdrawn through the cleanup flowline 699 is routed into the fluid analysis module 704 in the evaluation flowline 698 and a portion of the fluid withdrawn through the cleanup flowline 699 is routed into the fluid analysis module 704 in the cleanup flowline 699. The portion of the fluid withdrawn through the cleanup flowline 699 which is routed into the fluid analysis module 704 in the evaluation flowline 698 may be routed substantially simultaneously to routing of the portion of the fluid withdrawn through the cleanup flowline 699 which is routed into the fluid analysis module 704 in the cleanup flowline 699.

After self-calibration, commingled flow may be ended and independent monitoring performed by routing the fluid withdrawn in the evaluation flowline 698 into the fluid analysis module 704 in the evaluation flowline 698 and routing the fluid withdrawn in the cleanup flowline 699 into the fluid analysis module in the cleanup flowline 699. For example, the valves 720 may route the fluid withdrawn in the evaluation flowline 698 into the fluid analysis module 704 in the evaluation flowline 698 and may route the fluid withdrawn in the cleanup flowline 699 into the fluid analysis module in the cleanup flowline 699.

Figure 5:
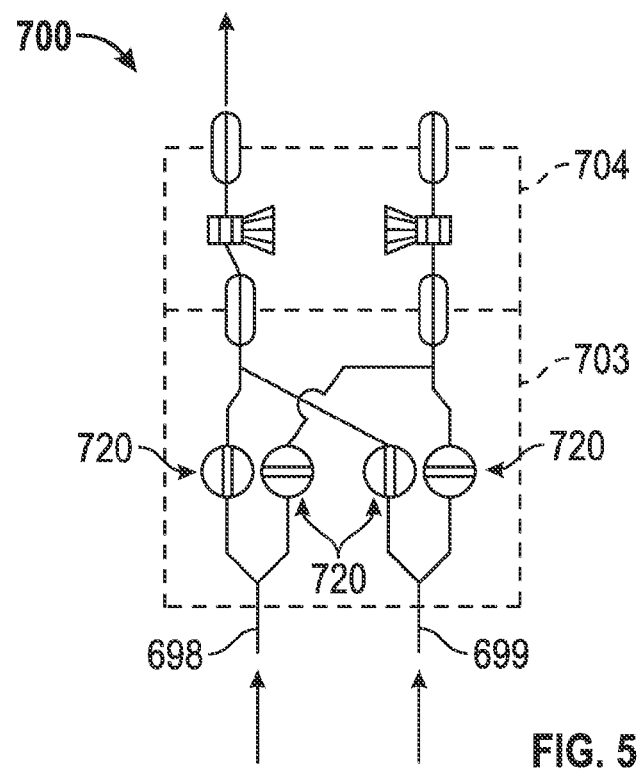
Figure 6:
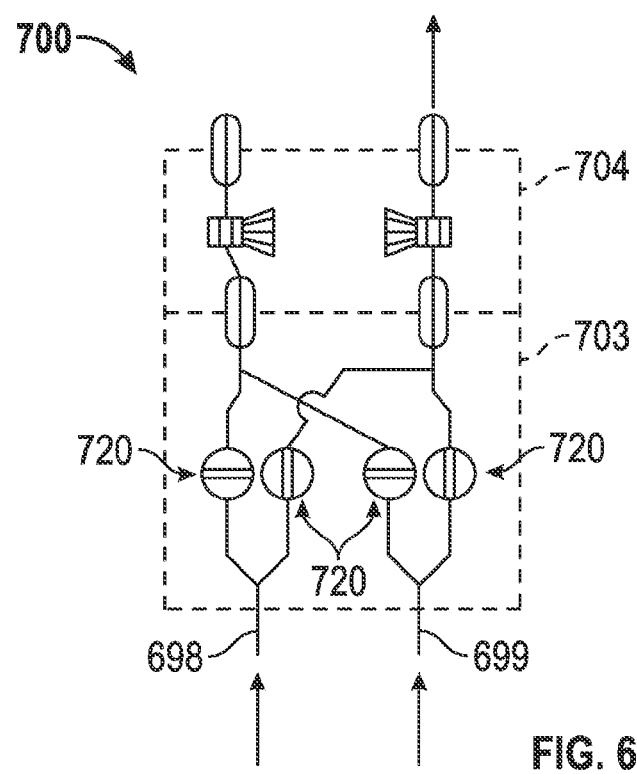

FIGS. 5 and 6 generally illustrate commingled flow diverted though a single flowline in the sampling tool 700. As shown in FIG. 5, the valves 720 may direct fluid in the evaluation flowline 698 into the subsequent section of the evaluation flowline 698 and may direct fluid in the cleanup flowline 699 into the evaluation flowline 698. The valves 720 may direct fluid in the evaluation flowline 698 into the subsequent section of the evaluation flowline 698 substantially simultaneously to directing fluid in the cleanup flowline 699 into the evaluation flowline 698. The fluid withdrawn through the evaluation flowline 698 may commingle in the evaluation flowline 698 with the fluid withdrawn through the cleanup flowline 699, and the commingled flow may be routed into the fluid analysis module 704 in the evaluation flowline 698.

As shown in FIG. 6, the valves 720 may direct fluid in the cleanup flowline 699 into the subsequent section of the cleanup flowline 699 and may direct fluid in the evaluation flowline 698 into the cleanup flowline 699. The valves 720 may direct fluid in the cleanup flowline 699 into the subsequent section of the cleanup flowline 699 substantially simultaneously to directing fluid in the evaluation flowline 698 into the cleanup flowline 699. The fluid withdrawn through the evaluation flowline 698 may commingle in the cleanup flowline 699 with the fluid withdrawn through the cleanup flowline 699, and the commingled flow may be routed into the fluid analysis module 704 in the cleanup flowline 699.

The embodiments depicted in FIGS. 5 and 6 may provide additional redundancy for the optical monitoring system. Then, commingled flow may be ended and independent monitoring performed by routing the fluid withdrawn in the evaluation flowline 698 into the fluid analysis module 704 in the evaluation flowline 698 and routing the fluid withdrawn in the cleanup flowline 699 into the fluid analysis module in the cleanup flowline 699. For example, the valves 720 may route the fluid withdrawn in the evaluation flowline 698 into the fluid analysis module 704 in the evaluation flowline 698 and may route the fluid withdrawn in the cleanup flowline 699 into the fluid analysis module in the cleanup flowline 699.

Figure 7:
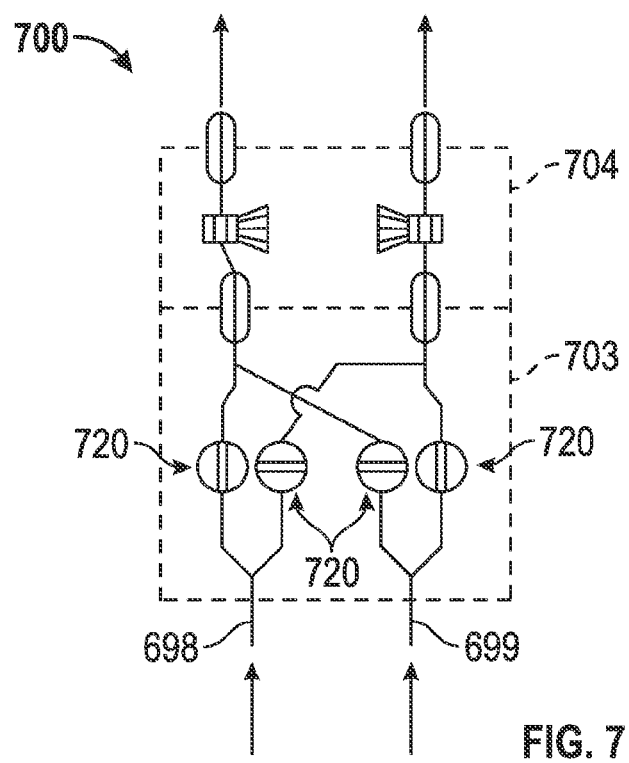
Figure 8:
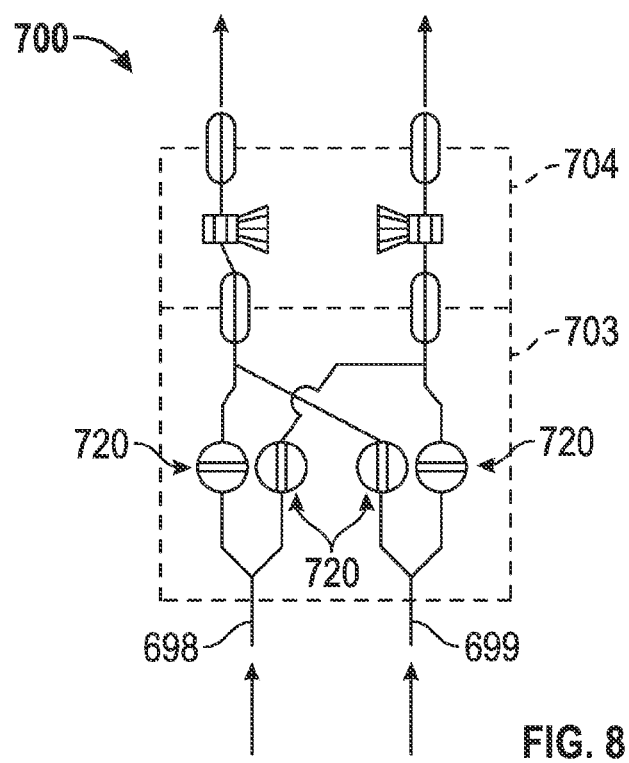

FIGS. 7 and 8 generally illustrate split flow during focused sampling with independent monitoring of the evaluation flowline 698 and the cleanup flowline 699. As shown in FIG. 7, the valves 720 may direct fluid in the evaluation flowline 698 into the subsequent section of the evaluation flowline 698 and may direct fluid in the cleanup flowline 699 into the subsequent section of the cleanup flowline 699. The valves 720 may direct fluid in the evaluation flowline 698 into the subsequent section of the evaluation flowline 698 substantially simultaneously to directing fluid in the cleanup flowline 699 into the subsequent section of the cleanup flowline 699. The fluid withdrawn through the evaluation flowline 698 may be routed into the fluid analysis module 704 in the evaluation flowline 698, and the fluid withdrawn through the cleanup flowline 699 may be routed into the fluid analysis module 704 in the cleanup flowline 699.

As shown in FIG. 8, the valves 720 may direct fluid in the cleanup flowline 699 into the evaluation flowline 698 and may direct fluid in the evaluation flowline 698 into the cleanup flowline 699. The valves 720 may direct fluid in the cleanup flowline 699 into the evaluation flowline 698 substantially simultaneously to directing fluid in the evaluation flowline 698 into the cleanup flowline 699. The fluid withdrawn through the evaluation flowline 698 may be routed into the fluid analysis module 704 in the cleanup flowline 699, and the fluid withdrawn through the cleanup flowline 699 may be routed into the fluid analysis module 704 in the evaluation flowline 698.

Figure 9:
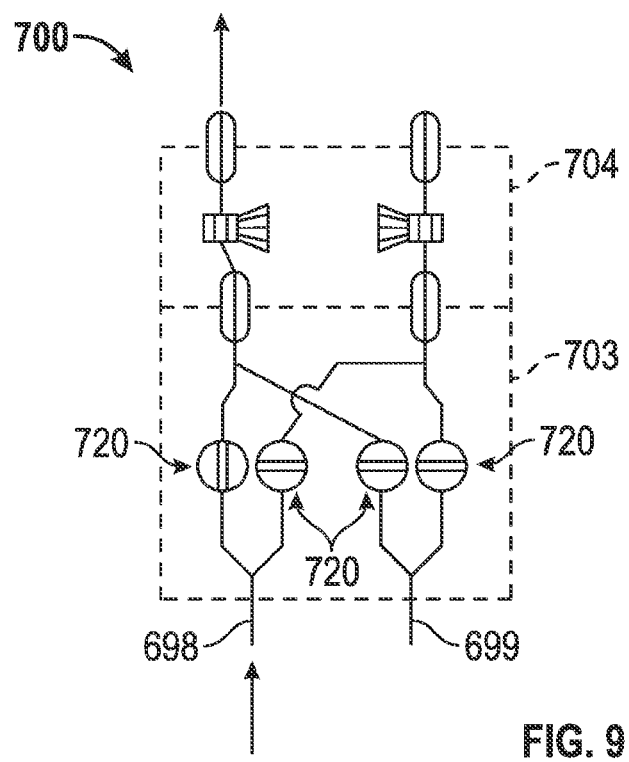
Figure 10:
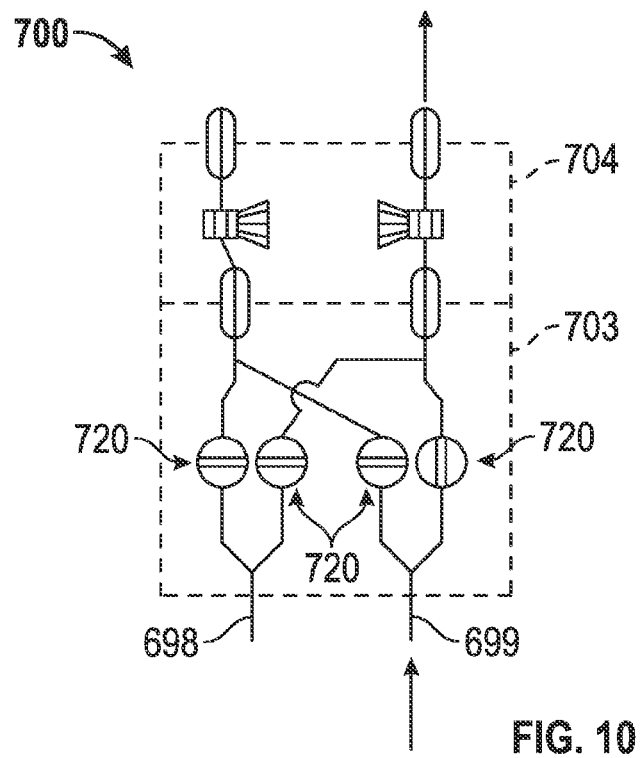

FIGS. 9-18 generally illustrate optional features of embodiments of the sampling tool 700. The optional features may be used for tool servicing and testing, may be used for problem mitigation, such as plugging, and may be used for any operation known to one skilled in the art. As generally illustrated in FIG. 9, the valves 720 may direct fluid in the evaluation flowline 698 into the subsequent section of the evaluation flowline 698. As generally illustrated in FIG. 10, the valves 720 may direct fluid in the cleanup flowline 699 into the subsequent section of the cleanup flowline 699.

Figure 11:
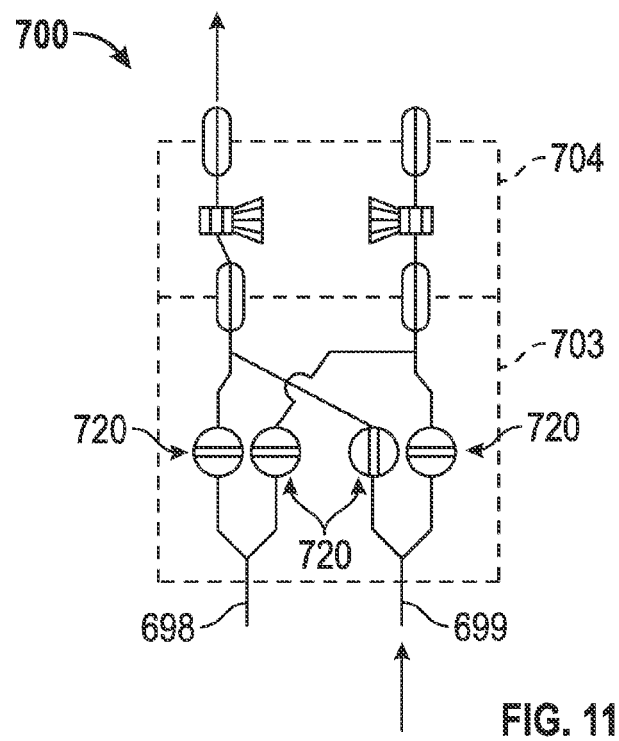
Figure 12:
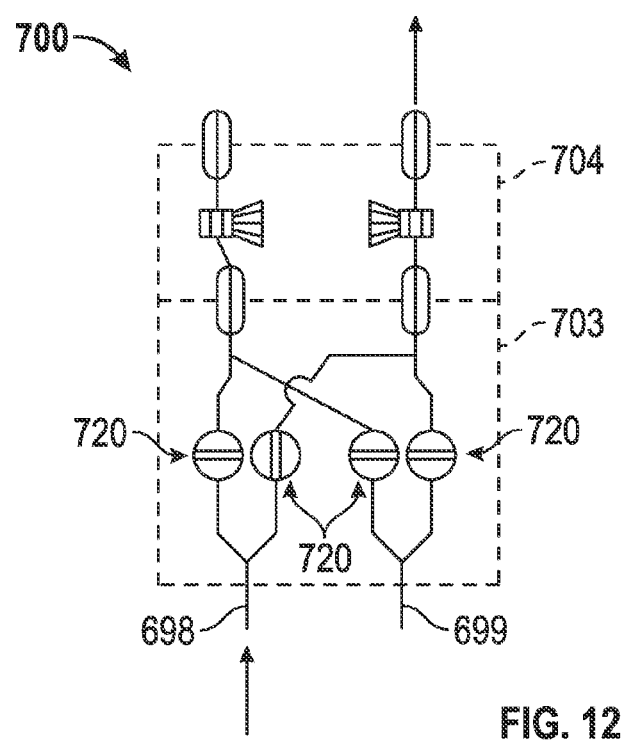
Figure 13:
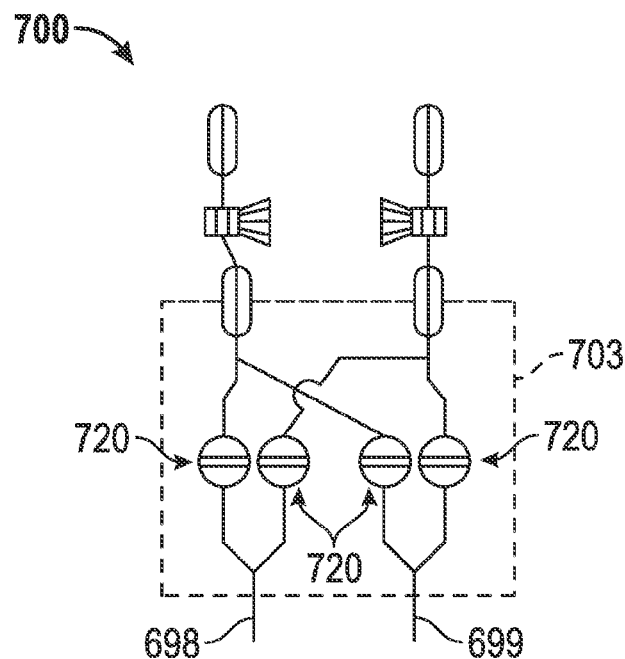
Figure 14:
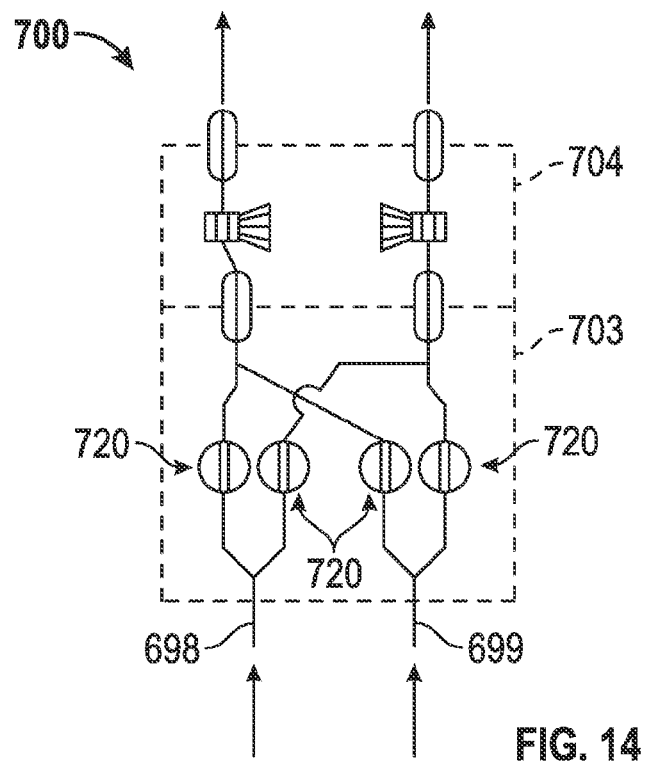

As generally illustrated in FIG. 11, the valves 720 may direct fluid in the cleanup flowline 699 into the evaluation flowline 698. As generally illustrated in FIG. 12, the valves 720 may direct fluid in the evaluation flowline 698 into the cleanup flowline 699. As generally illustrated in FIG. 13, the valves 720 may close to isolate the focused probe module 702 from the downstream components of the sampling tool 700. FIG. 14 generally illustrates a commingled flow with the valves 720 open.

Figure 15:
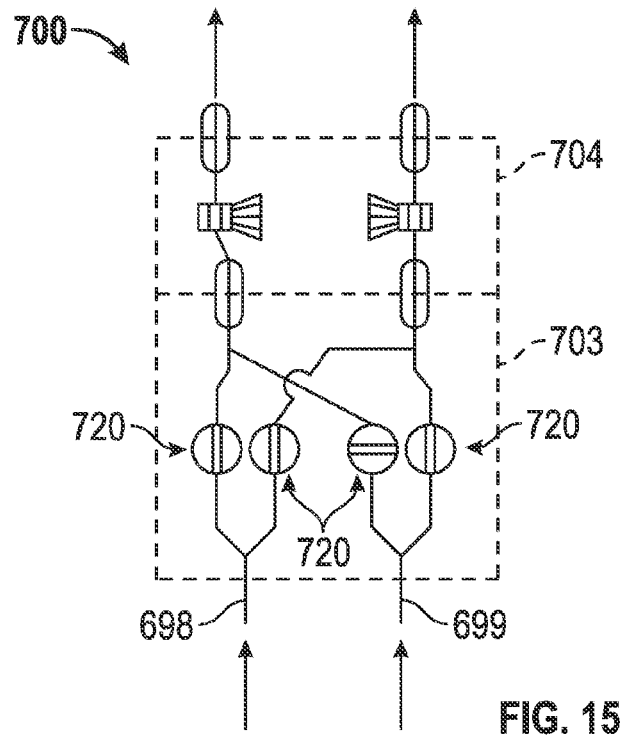

FIG. 15 generally illustrates a commingled flow with an isolated evaluation flowline 698. The valves 720 may direct fluid in the evaluation flowline 698 into the cleanup flowline 699 and the subsequent section of the evaluation flowline 698. The valves 720 may direct fluid in the cleanup flowline 699 into the subsequent section of the cleanup flowline 699.

Figure 16:
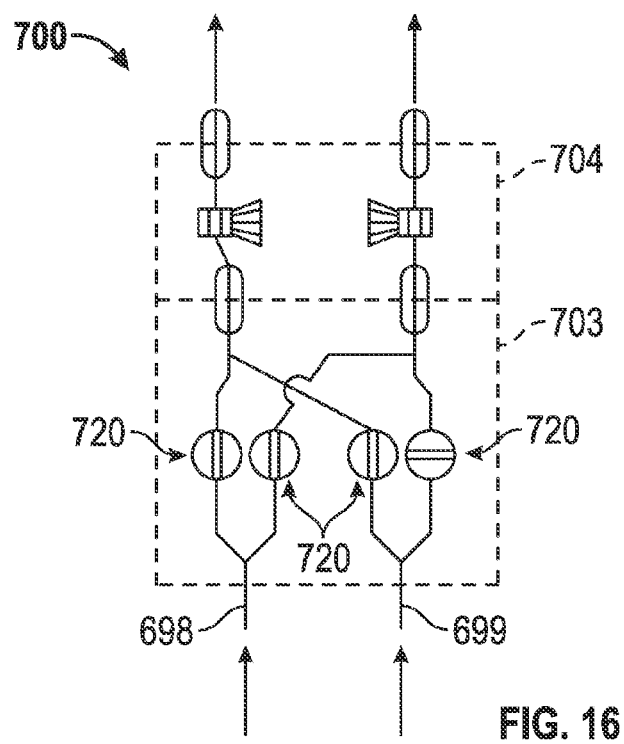
Figure 17:
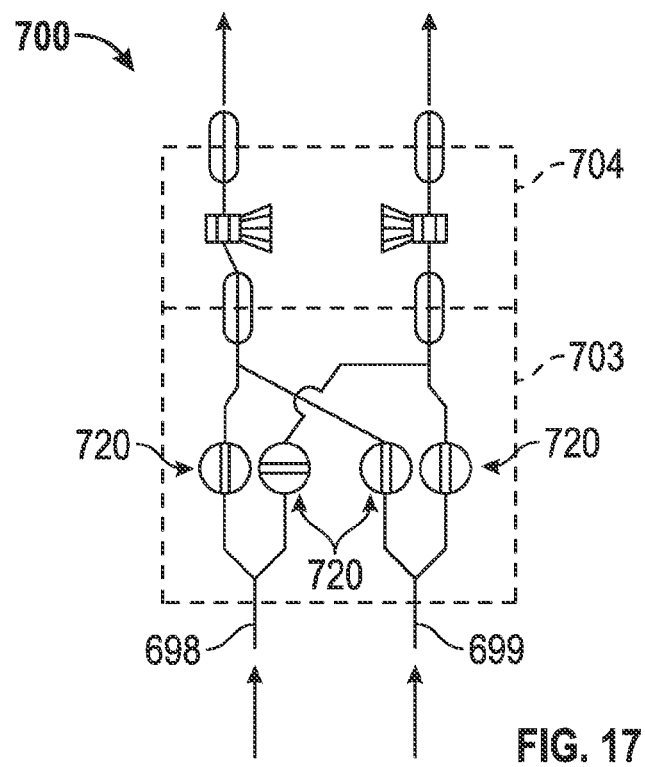
Figure 18:
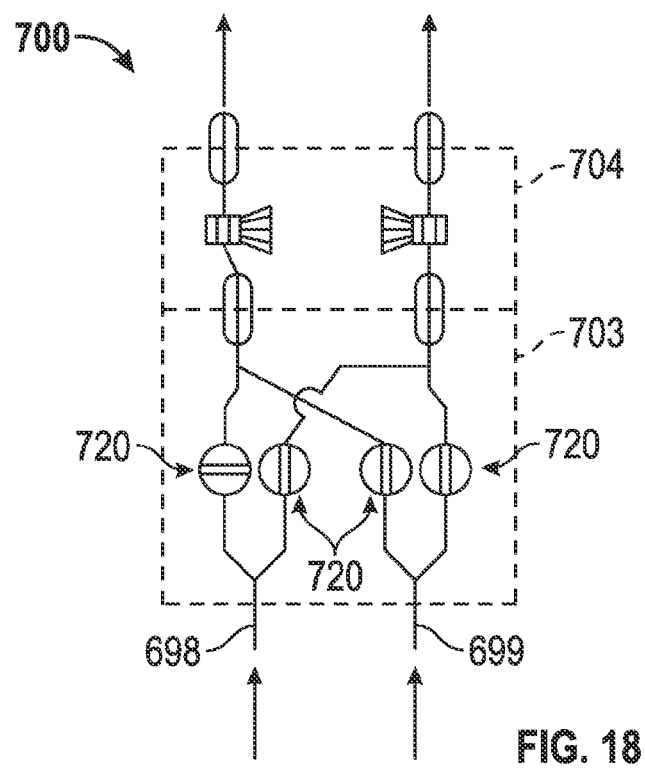

FIG. 16 generally illustrates that the valves 720 may direct fluid in the evaluation flowline 698 into the cleanup flowline 699 and the subsequent section of the evaluation flowline 698. The valves 720 may direct fluid in the cleanup flowline 699 into the evaluation flowline 698. FIG. 17 generally illustrates that the valves 720 may direct fluid in the cleanup flowline 699 into the evaluation flowline 698 and the subsequent section of the cleanup flowline 699. The valves 720 may direct fluid in the evaluation flowline 698 into the subsequent section of the evaluation flowline 699. FIG. 18 generally illustrates that the valves 720 may direct fluid in the cleanup flowline 699 into the evaluation flowline 698 and the subsequent section of the cleanup flowline 699. The valves 720 may direct fluid in the evaluation flowline 698 into the cleanup flowline 699.

Figure 19:
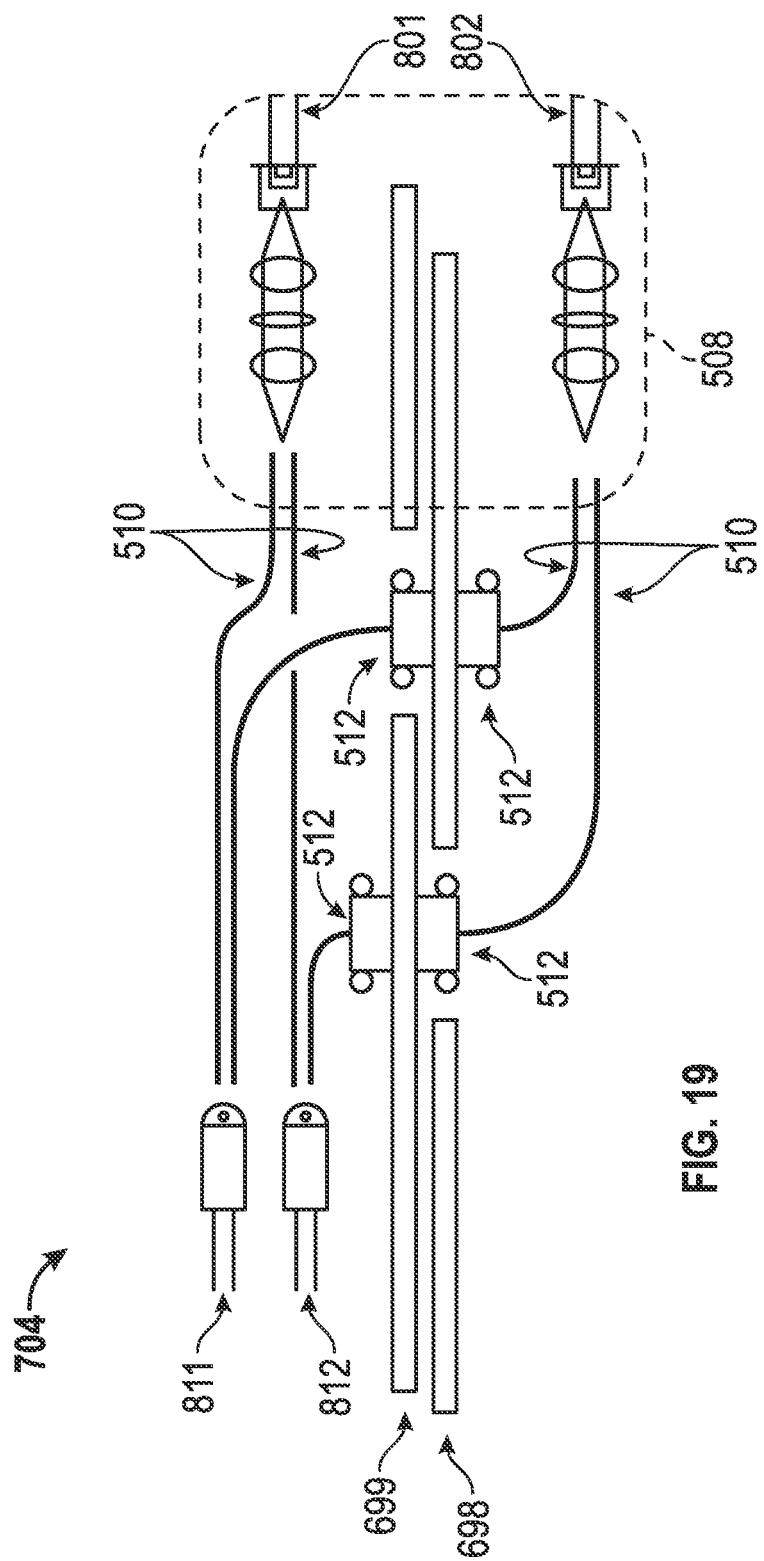
Figure 20:
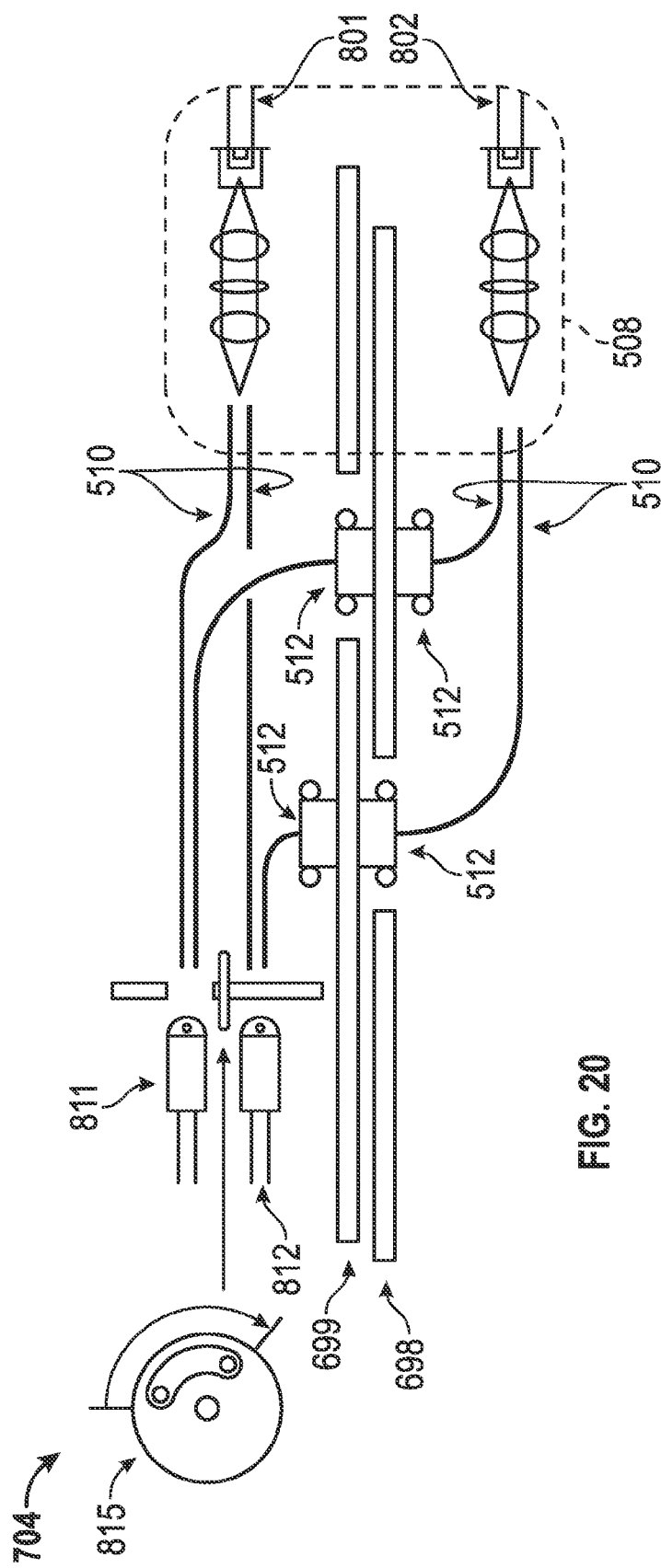

FIGS. 19 and 20 generally illustrate embodiments of the fluid analysis module 704 in which a source optic transducer 801 and a sample optic transducer 802 are at least partially shared between an evaluation flowline sensor and a cleanup flowline sensor. The fluid analysis module 704 may be the single optical fluid analyzer module 500 and/or another optical fluid analyzer module. The source optic transducer 801 and/or the sample optic transducer 802 may be a lens and a photodiode. The source optic transducer 801 and/or the sample optic transducer 802 may be provided by the spectrometer 508.

A first lamp 811 and a second lamp 812 may emit light at different wavelengths. The source optic transducer 801 may monitor the strength of the light emitted by the first lamp 811 and/or the second lamp 812. The second optic transducer 802 may measure the light transmitted through the evaluation flowline 698 or the cleanup flowline 699 at different wavelengths.

The first lamp 811 and/or the second lamp 812 may face the bundle of optical fibers 508 which may direct light to the evaluation flowline 698 and/or the cleanup flowline 699. Referring to FIG. 19, when the first lamp 811 is inactive, the second lamp 812 may emit light, and measurement may be performed on the fluid in one of the evaluation flowline 698 and the cleanup flowline 699. When the second lamp 812 is inactive, the first lamp 811 may emit light, and measurement may be performed on the fluid in the other one of the evaluation flowline 698 and the cleanup flowline 699. The source optic transducer 801 and the sample optic transducer 802 may have any number of channels; in an embodiment, the source optic transducer 801 may have two channels, and the sample optic transducer 802 may have five channels.

FIG. 20 generally illustrates that an optical signal may be multiplexed using a disk wheel 815. In an embodiment, a cable router may be used additionally or alternatively to the disk wheel 815. The first lamp 811 and the second lamp 812 may emit light, and the disk wheel 815 may direct the light of one of the first lamp 811 and the second lamp 812 to the bundle of optical fibers 508. When the disk wheel 815 directs light from the first lamp 811 to the bundle of optical fibers 508, measurement may be performed on the fluid in one of the evaluation flowline 698 and the cleanup flowline 699. When the disk wheel 815 directs light from the second lamp 812 to the bundle of optical fibers 508, measurement may be performed on the fluid in the other one of the evaluation flowline 698 and the cleanup flowline 699. The source optic transducer 801 and the sample optic transducer 802 may have any number of channels; in an embodiment, the source optic transducer 801 may have three channels, and the sample optic transducer 802 may have ten channels.

Although FIGS. 19 and 20 may use the spectrometer 508 and/or another optical fluid analyzer, the fluid analysis module 704 may use another fluid sensor, such as, for example, a density sensor, a viscosity sensor, a permittivity sensor, and/or the like. The dual flowline architecture with two or more sensors collated may be used to calibrate the sensors. A calibration may be conducted in-shop using known fluids with known fluid properties or conducted in-situ by diverting the same fluid to the sensors located in different flowlines. Repeated calibrations of the two sensors or exact working equations based on the principle of physics for which no calibration is required, for example, the vibrating wire viscometer, may be performed. To ensure that the same fluid is tested by the sensors during a calibration, the flowlines may be provided with the flowline routing module 703 upstream of the sensors and/or adjacent to the sensors. Fluid pumped from the formation in one of the two flowlines may be routed intermittently to both sensors to obtain a calibration point, such as, for example, every five seconds.

Figure 21:
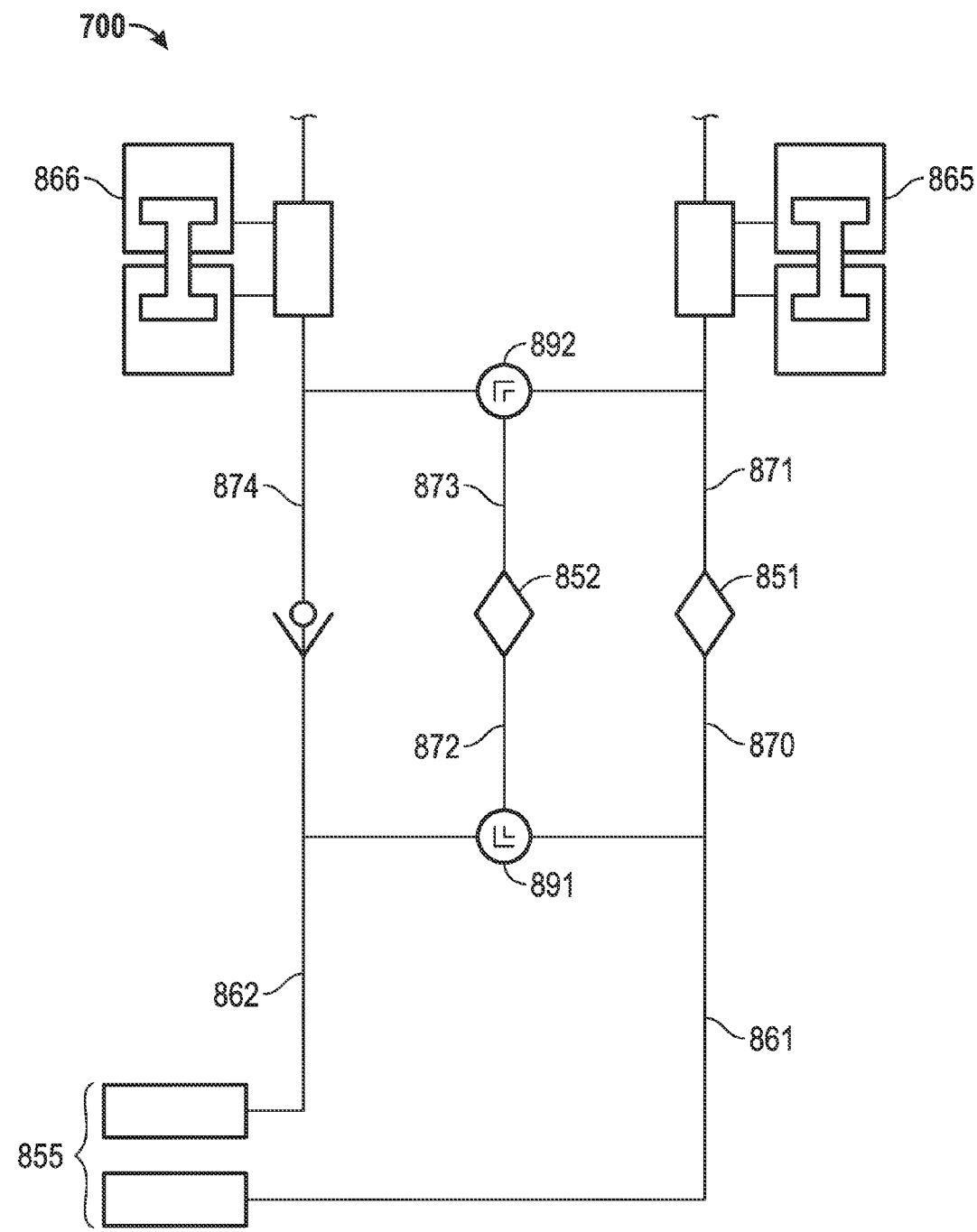

FIG. 21 generally illustrates an embodiment of the sampling tool 700 which may use the flowline routing module 703 to selectively divert fluid from one flowline to a first contamination sensor 851 and/or a second contamination sensor 852. When the same fluid is analyzed by the first contamination sensor 851 and the second contamination sensor 852, any drift between the first contamination sensor 851 and the second contamination sensor 852 that has not been eliminated by sharing transducers may be measured, may be recorded and/or may be accounted for by processing. For example, drift caused by variations of the light path through the optical windows 512 may be may be measured, may be recorded and/or may be accounted for by processing.

As shown, a sample flowline 861, such as, for example, the evaluation flowline 698, and a guard flowline 862, such as, for example, the cleanup flowline 699, may be connected to inlets 855. Fluid may pumped in the sample flowline 861 via a first reciprocating pump 865 and may travel by the first contamination sensor 851 via flowline portions 870 and 871. Fluid may pumped in the guard flowline 862 via a second reciprocating pump 866 and may travel by the second contamination sensor 852 via flowline portions 872 and 873.

A first distribution valve 891 and a second distribution valve 892 may be actuated substantially simultaneously to connect the second contamination sensor 852 to the guard flowline 862 or, as shown in the example in FIG. 21, the sample flowline 861. Periodically, such as, for example, each five minutes approximately, the first distribution valve 891 and the second distribution valve 892 may be switched substantially simultaneously for a short period of time, such as, for example, when the stroke direction of the first reciprocating pump 865 and/or the second reciprocating pump 866 is reversed. A bypass flowline portion 874 may be provided to continue pumping fluid in the guard flowline 862 when the first contamination sensor 851 and the second contamination sensor 852 are fluidly connected to the sample flowline 861. FIG. 21 merely depicts an example of a fluid routing system, and other routing system configurations may be used, such as, for example, to divert fluid from the guard flowline 862 to the first contamination sensor 851 and the second contamination sensor 852.

Analysis may compensate for the different time of flow in the sample flowline 861 and the guard flowline 862 of the sampling tool 700. For example, interpretation techniques may involve the properties of the fluids entering the ports of the sampling tool at a particular instant t. The fluid may be pumped in one of the flowlines at a rate $Q_1$ and in the other flowline at a rate $Q_2$. The volumes of flowline between the inlets of the sampling tool 700 and the contamination sensors 851, 852 may be V. The properties of the fluid entering the sampling tool 700 at a particular instant t may be measured after a delay $T_1=V/Q_1$ at one of the contamination sensors 851, 852 and a delay $T_2=V/Q_2$ at the other one of the contamination sensors 851, 852.

A program running on a processor in the sampling tool 700 may acquire the pump rates of the first reciprocating pump 865 and/or the second reciprocating pump 866 in real-time, may use stored values of the flowline volumes to compute flow delays, and/or may analyze fluid properties measured with the two contamination sensors 851, 852 after correction of the flow delays. Flowmeters disposed on the sample flowline 861 and the guard flowline 862 may be used alternatively or additionally relative to the measurements of the pump rates.

Figure 22:
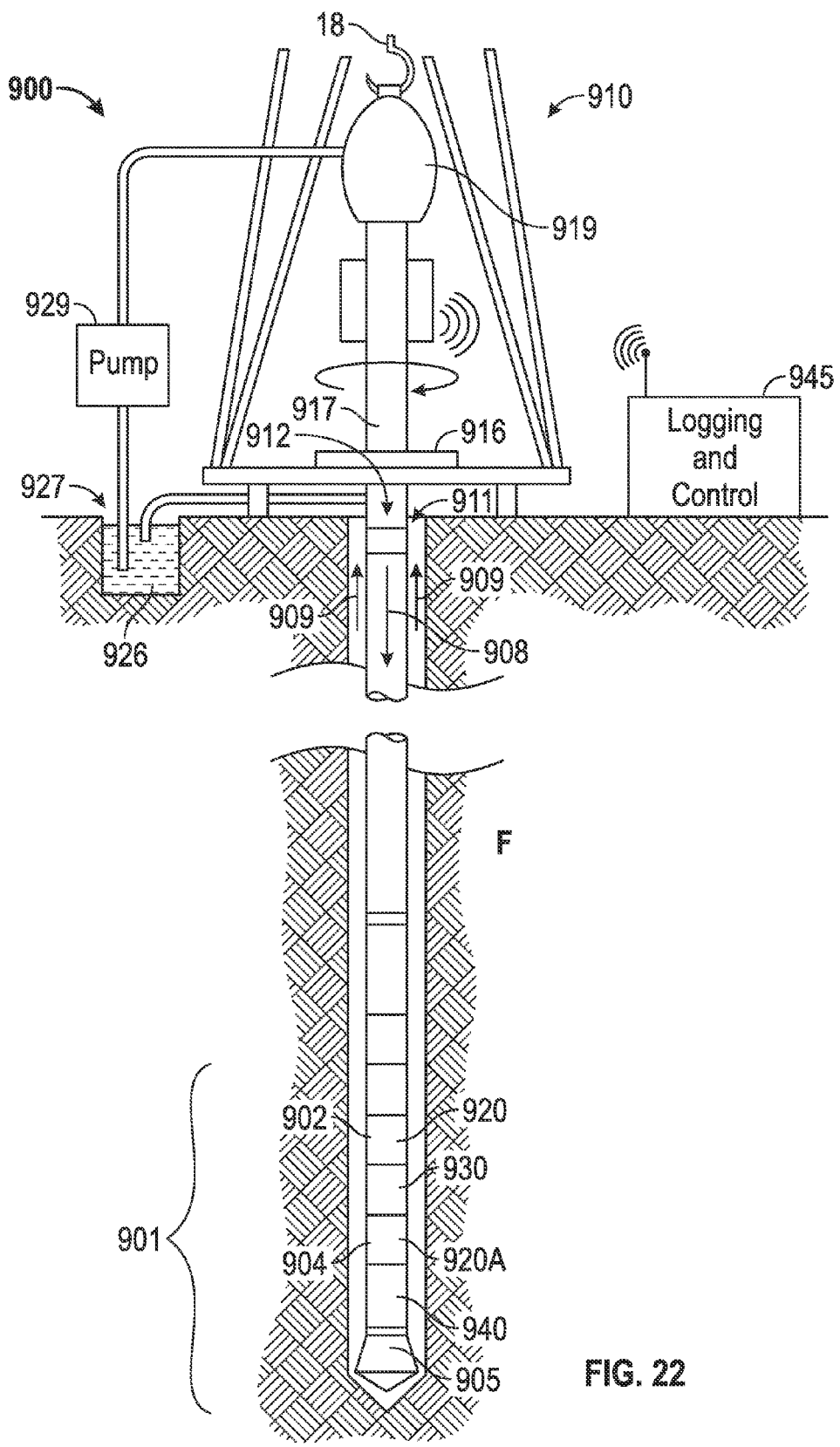
FIG. 22 generally illustrates a schematic view of an example wellsite drilling system.

FIG. 22 generally illustrates an example wellsite drilling system 900 which may be employed onshore and/or offshore and which may implement the example fluid control modules described herein. In the example wellsite drilling system 900, a borehole 911 may be formed in a subsurface formation F by rotary and/or directional drilling.

As generally illustrated in FIG. 22, a drillstring 912 may be suspended in the borehole 911 and may have a bottom-hole assembly (BHA) 901 having a drill bit 905 at its lower end. A surface system may includes a platform and derrick assembly 910 positioned over the borehole 911. The derrick assembly 910 may include a rotary table 916, a kelly 917, a hook 918 and a rotary swivel 919. The drillstring 912 may be rotated by the rotary table 916 which engages the kelly 917 at an upper end of the drillstring 912. The drillstring 912 may be suspended from the hook 918 which may be attached to a traveling block (not shown). Additionally or alternatively, a top drive system may be used.

The surface system may include drilling fluid 926, commonly referred to in the industry as "mud." The drilling fluid 926 may be stored in a pit 927. A pump 929 may deliver the drilling fluid 926 to the interior of the drillstring 912 via a port in the rotary swivel 919 so that the drilling fluid 926 may flow downwardly through the drillstring 912 as indicated by the directional arrow 908. The drilling fluid 926 may exit the drillstring 912 via ports in the drill bit 905 and then may circulate upwardly through the annulus region between the outside of the drillstring 912 and the wall of the borehole 911 as indicated by the directional arrows 909. The drilling fluid 926 may lubricate the drill bit 905, may carry formation cuttings up to the surface as the drilling fluid 926 returns to the pit 927 for recirculation, and may create a mudcake layer (not shown), such as a filter cake, on the walls of the borehole 911.

The BHA 901 may include, among other components, any number and/or types of logging-while-drilling (LWD) modules or tools, two of which are designated by reference numerals 920 and 920A, and/or measuring-while-drilling (MWD) modules, one of which is designated by reference numeral 930. The BHA 901 may include a rotary-steerable system or mud motor 940 and the drill bit 905. The MWD module 130 may measure the azimuth and the inclination of the drill bit 905 that may be used to monitor the borehole trajectory.

The example LWD tools 920 and 920A may be housed in drill collars 902 and 904, respectively. The drill collars 902 and 904 may contain any number of logging tools and/or fluid sampling devices. The example LWD tools 920 and 920A may include capabilities for measuring, processing and/or storing information, as well as for communicating with the MWD module 930 and/or directly with the surface equipment, such as, for example, a logging and control computer 945.

The logging and control computer 945 may include a user interface that enables parameters to be input and/or outputs to be displayed. While the logging and control computer 945 is depicted uphole and adjacent the wellsite system, at least portion of the logging and control computer 945 may be positioned in the BHA 901 and/or in a remote location.

Figure 23:
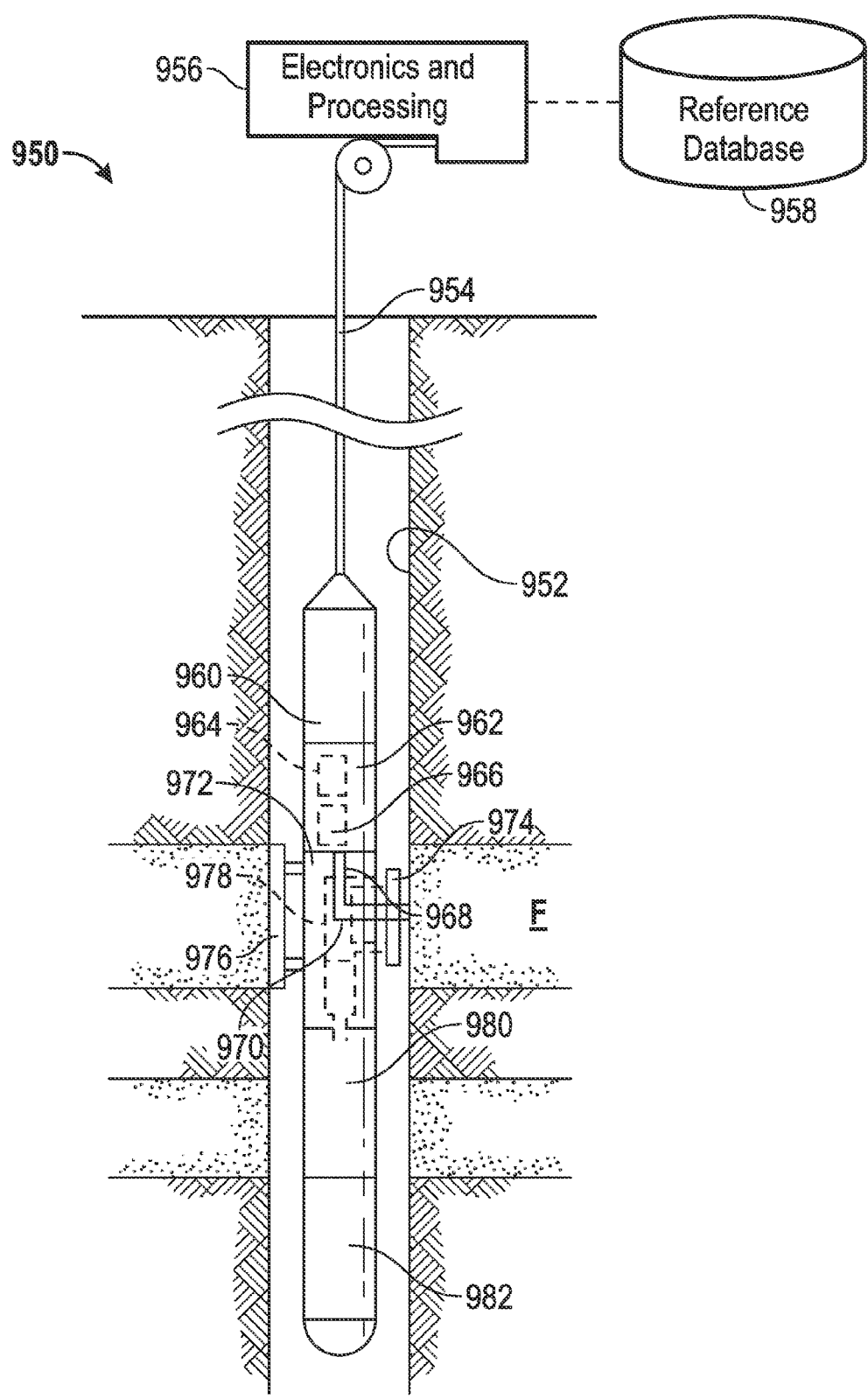
FIG. 23 generally illustrates a schematic view of an example wireline tool which may employ a single optical fluid analyzer in accordance with one or more aspects of the present disclosure.

FIG. 23 depicts an example wireline tool 950 that may be used to extract and analyze formation fluid samples and which may implement the flowline routing module 703 and/or the fluid analysis module 704 described herein. The example wireline tool 950 may be used to analyze formation fluid samples by, for example, selectively controlling fluid flow through the wireline tool 950. The example wireline tool 950 may be the sampling tool 700.

As shown in FIG. 23, the example wireline tool 950 may be suspended in a borehole or wellbore 952 from the lower end of a multiconductor cable 954 spooled on a winch at the surface. At the surface, the cable 954 may be communicatively coupled to an electronics and processing system 956 which may include or be communicatively coupled to a database 958, such as, for example, a memory module, that may be used to store measurement values obtained using the examples described herein. The example wireline tool 950 may include an elongated body 960 having a collar 962. A downhole control system 964 in and/or connected to the collar 962 may be configured to control extraction of formation fluid from the formation F, perform measurements on the extracted fluid, and/or control the flowline routing module 703 to control fluid flow though the wireline tool 950.

The example wireline tool 950 may have a formation tester 972 having a selectively extendable fluid admitting assembly 974 and may have a selectively extendable tool anchoring member 976 that may be arranged on opposite sides of the elongated body 960. The fluid admitting assembly 974 may be configured to selectively isolate selected portions of the wall of the wellbore 952 to fluidly couple to the adjacent formation F and/or draw fluid samples from the formation F. The formation tester 972 may includes a fluid analysis module 978, such as, for example, the fluid analysis module 704, through which the obtained fluid samples may flow. The sample fluid may thereafter be expelled through a port (not shown) and/or may be sent to one or more fluid collecting chambers 980 and 982, each of which may be the sample chamber 722. The one or more fluid collecting chambers 980 and 982 may analyze the formation fluid samples and/or may receive and retain the formation fluid samples for subsequent testing at the surface or a testing facility.

The electronics and processing system 956 and/or the downhole control system 964 may be configured to control the fluid admitting assembly 974 to draw fluid samples from the formation F. The electronics and processing system 956 and/or the downhole control system 964 may be configured to control the fluid analysis module 978 to measure the fluid samples. In some embodiments, the fluid analysis module 978 may be configured to analyze the measurement data of the fluid samples. In other embodiments, the fluid analysis module 978 may be configured to generate and store the measurement data and subsequently communicate the measurement data to the surface for analysis at the surface. Although the downhole control system 964 is shown as separate from the formation tester 972, in some embodiments the downhole control system 964 may be implemented in the formation tester 972.

The example wireline tool 950 may be used with the flowline routing module 703 and/or the fluid analysis module 704 to control a flow of fluid through and/or between the evaluation flowline 698 and/or the cleanup flowline 699. For example, the formation tester 972 may include one or more sensors, fluid analyzers and/or fluid measurement units which may be disposed adjacent the evaluation flowline 698 and/or the cleanup flowline 699 and which may be controlled by the downhole control system 964 and/or the electronics and processing system 956. The composition of and/or a characteristic of fluid samples extracted from the formation F may be determined.

A drillstring such as that shown in FIG. 22 and a wireline tool such as that shown in FIG. 23 may be used to implement the flowline routing module 703 and/or the fluid analysis module 704; however, the flowline routing module 703 and/or the fluid analysis module 704 may be implemented with any other type of wellbore conveyance.

The preceding description has been presented with reference to present embodiments. Persons skilled in the art and technology to which this disclosure pertains will appreciate that alterations and changes in the described structures and methods of operation can be practiced without meaningfully departing from the principle and scope of the disclosure. Accordingly, the foregoing description should not be read as pertaining only to the precise structures described and shown in the accompanying drawings, but rather should be read as consistent with and as support for the following claims, which are to have their fullest and fairest scope.

Moreover, means-plus-function clauses in the claims cover the structures described herein as performing the recited function and not only structural equivalents but also equivalent structures. Thus, a nail and a screw may not be structural equivalents because a nail employs a cylindrical surface to secure parts together and a screw employs a helical surface, but in the environment of fastening parts, a nail may be the equivalent structure to a screw. Applicant expressly intends to not invoke 35 U.S.C. §112, paragraph 6, for any of the limitations of the claims herein except for claims which explicitly use the words "means for" with a function.

We claim:

1. An optical fluid analyzer tool, comprising:
   inlets for obtaining fluid;
   an evaluation flowline connected to a first inlet and a flowline routing module;
   a cleanup flowline connected to a second inlet and the flowline routing module;
   a subsequent section of the evaluation flowline connected to the flowline routing module;
   a subsequent section of the cleanup flowline connected to the flowline routing module;
   a single optical fluid analyzer connected to the subsequent section of the cleanup flowline and the subsequent section of the evaluation flowline, wherein the single optical fluid analyzer comprises:
      a lamp;
      a first optical fiber bundle configured to convey optical illumination from the lamp to first optical windows of the subsequent section of the evaluation flowline;

a second optical fiber bundle configured to convey optical illumination from the lamp to second optical windows of the subsequent section of the cleanup flowline;
a third optical fiber bundle configured to convey light from the first optical windows to a spectrometer; and
a fourth optical fiber bundle configured to convey light from the second optical windows to the spectrometer; and
wherein the flowline routing module is located between the single optical fluid analyzer and the inlets and is configured to selectively direct fluid from the evaluation flowline into the cleanup flowline, selectively direct fluid from the cleanup flowline to the evaluation flowline, selectively direct fluid from the evaluation flowline into a subsequent section of the evaluation flowline, and selectively direct fluid from the cleanup flowline into a subsequent section of the cleanup flowline.

2. The optical fluid analyzer tool of claim 1 further comprising:
a packer configured to abut a geotechnical formation to withdraw the fluid from the geotechnical formation.

3. The optical fluid analyzer tool of claim 1 further comprising:
a relief valve connected to the evaluation flowline and the cleanup flowline.

4. The optical fluid analyzer tool of claim 1 further comprising:
a first pump module for drawing fluid into the inlets.

5. The optical fluid analyzer tool of claim 1 wherein the flowline routing module splits flows, commingles flows and isolates flows between the evaluation flowline and the cleanup flowline.

6. The optical fluid analyzer tool of claim 1 wherein the flowline routing module comprises four valves.

7. The optical fluid analyzer tool of claim 1 further comprising:
a port configured to deliver a sample of fluid from the optical fluid analyzer tool to an external environment of the optical fluid analyzer tool.

8. The optical fluid analyzer tool of claim 1 further comprising:
a sample chamber connected to the evaluation flowline and the cleanup flowline.

9. The optical fluid analyzer tool of claim 8 further comprising:
a fluid isolation valve connected to the sample chamber, the fluid in the evaluation flowline and the cleanup flowline isolated from the sample chamber by the fluid isolation valve.

10. A method of analyzing a geotechnical formation, comprising:
withdrawing a fluid from the geotechnical formation through an evaluation flowline and a cleanup flowline;
routing the fluid through a flowline analysis module connected to a subsequent section of the cleanup flowline and a subsequent section of the evaluation flowline, wherein the flowline analysis module comprises a single optical fluid analyzer, the single optical fluid analyzer comprising:
a lamp;
a first optical fiber bundle configured to convey optical illumination from the lamp to first optical windows of the subsequent section of the evaluation flowline;
a second optical fiber bundle configured to convey optical illumination from the lamp to second optical windows of the subsequent section of the cleanup flowline;
a third optical fiber bundle configured to convey light from the first optical windows to a spectrometer; and
a fourth optical fiber bundle configured to convey light from the second optical windows to the spectrometer; and
calibrating the fluid analysis module based on at least one measurement obtained by the single optical fluid analyzer in the fluid analysis module.

11. The method of claim 10 wherein the at least one measurement on which calibration of the fluid analysis module is based is obtained by the single optical fluid analyzer when the fluid withdrawn through the evaluation flowline is routed into the fluid analysis module in the evaluation flowline and the fluid withdrawn through the cleanup flowline is routed into the fluid analysis module in the evaluation flowline.

12. The method of claim 10 wherein the at least one measurement on which calibration of the fluid analysis module is based is obtained by the single optical fluid analyzer when the fluid withdrawn through the evaluation flowline is routed into the fluid analysis module in the cleanup flowline and the fluid withdrawn through the cleanup flowline is routed into the fluid analysis module in the cleanup flowline.

13. The method of claim 10 wherein the at least one measurement on which calibration of the fluid analysis module is based is obtained by the single optical fluid analyzer when the fluid analysis module receives commingled flow in the evaluation flowline and commingled flow in the cleanup flowline, wherein a portion of the fluid in the evaluation flowline is routed into the cleanup flowline to form the commingled flow in the cleanup flowline and a portion of the fluid in the cleanup flowline is routed into the evaluation flowline to form the commingled flow in the evaluation flowline.

14. The method of claim 13 further comprising:
ending commingled flow by routing the fluid withdrawn in the evaluation flowline into the fluid analysis module in the evaluation flowline and routing the fluid withdrawn in the cleanup flowline into the fluid analysis module in the cleanup flowline.

15. A method of analyzing a geotechnical formation, comprising:
withdrawing a fluid from the geotechnical formation through an evaluation flowline and a cleanup flowline;
configuring a fluid routing module to perform at least one of directing fluid from the evaluation flowline into the cleanup flowline, directing fluid from the cleanup flowline to the evaluation flowline, directing fluid from the evaluation flowline into a subsequent section of the evaluation flowline, and directing fluid from the cleanup flowline into a subsequent section of the cleanup flowline; and
calibrating a fluid analysis module connected to the subsequent section of the cleanup flowline and the subsequent section of the evaluation flowline based on at least one measurement obtained by the fluid analysis module, wherein the fluid analysis module comprises a single optical fluid analyzer, the single optical fluid analyzer comprising:
a lamp;
a first optical fiber bundle configured to convey optical illumination from the lamp to first optical windows of the subsequent section of the evaluation flowline;

a second optical fiber bundle configured to convey optical illumination from the lamp to second optical windows of the subsequent section of the cleanup flowline;

a third optical fiber bundle configured to convey light from the first optical windows to a spectrometer; and a fourth optical fiber bundle configured to convey light from the second optical windows to the spectrometer.

16. The method of claim 15 wherein the fluid routing module routs fluid from the evaluation flowline into the cleanup flowline substantially simultaneously to routing fluid from the cleanup flowline into the evaluation flowline.

17. The method of claim 15 wherein the fluid routing module routs fluid from the evaluation flowline into the cleanup flowline substantially simultaneously to routing fluid from the cleanup flowline into the subsequent section of the cleanup flowline.

18. The method of claim 15 wherein the fluid routing module routs fluid from the cleanup flowline into the evaluation flowline substantially simultaneously to routing fluid from the evaluation flowline into the subsequent section of the evaluation flowline.

* * * * *